(12) United States Patent
Paskavitz et al.

(10) Patent No.: US 7,658,912 B2
(45) Date of Patent: Feb. 9, 2010

(54) SPATIAL EVOLUTION OF NEURAL ACTIVITY

(75) Inventors: James F. Paskavitz, Holden, MA (US); Larry H. Sweet, Providence, RI (US)

(73) Assignee: University of Massachusetts, Boston, MA (US)

( * ) Notice: Subject to any disclaimer, the term of this patent is extended or adjusted under 35 U.S.C. 154(b) by 707 days.

(21) Appl. No.: 10/871,745

(22) Filed: Jun. 18, 2004

(65) Prior Publication Data

US 2005/0053550 A1    Mar. 10, 2005

Related U.S. Application Data

(60) Provisional application No. 60/480,034, filed on Jun. 20, 2003.

(51) Int. Cl.
*A61K 49/00* (2006.01)
(52) U.S. Cl. .................. 424/9.2; 424/9.1; 424/1.11
(58) Field of Classification Search ............... 424/1.11, 424/1.65, 9.1, 9.2, 9.3, 9.4, 9.5, 9.6, 9.7, 424/9.8
See application file for complete search history.

(56) References Cited

U.S. PATENT DOCUMENTS

| 7,166,438 | B2 * | 1/2007 | Patchev et al. ............... 435/7.8 |
| 2005/0019261 | A1 * | 1/2005 | Albrecht et al. ............... 424/9.2 |

OTHER PUBLICATIONS

Panisset et al (2002), Journal of Neural Transmission, vol. 109, Nos. 7-8, pp. 1089-1104.*
Paskavitz JF, Sweet LH, Wellen J, Helmer KG, Cohen RA. "Dynamic Changes in Brain Volumes of Activation During Sustained Working Memory Observed with fMRI," International Neuropsychological Society Annual Meeting, 2003, Honolulu, Hawaii, JINS, 2003, 9(2); 321.
Braver, et al. "A Parametric Study of Prefrontal Cortex Involvement in Human Working Memory," Neuroimage 1997, 5:49-62.
Cox, "AFNI Software for Analysis and Visualization of Functional Magnetic Resonance Neuroimages," Compt. Biomed. Res., 1996, 29:129-173.
Rao, et al. "Functional magnetic resonance imaging of complex human movements," Neurology 43:2311-2318 (1993).
Wellen, J., "Characterization of Soft-Tissue Response to Mechanical Loading Using Nuclear Magnetic Resonance (NMR) and Functional Magnetic Resonance (fMRI) of Neuronal Activity During Sustained Cognitive-Stimulus Paradigms," PhD thesis, Worcester Polytechnic Institute, Defended May 2003, Published Jun. 2003, Chapter 6, "Functional Brain Imaging," 7 pages and Chapter 7 "Dynamic Changes in Neural Network Activation Patterns," 21 pages.
"Brain Mapping: the methods" 2d ed. Chapter 22, "Statistics I: Experimental Design and Statistical Parametric Mapping," contributed by Karl J. Friston, (2002), pp. 605-631.
M. Samuel, et al., "Exploring the temporal nature of hemodynamic responses of cortical motor areas using functional MRI," 1998, Neurology 1998; 51: 1567-1575.
J.W. Fisher, III, et al. "Adaptive Entropy Rates for fMRI Time-Series Analysis," MICCAI 2001, 4$^{th}$ Int'l Conf., Utrecht, Netherlands, Oct. 14-17, 2001.

* cited by examiner

*Primary Examiner*—D L Jones
(74) *Attorney, Agent, or Firm*—Fish & Richardson P.C.

(57) ABSTRACT

A method for identifying a candidate drug includes administering a test compound to test subjects and having the test subjects perform a sustained task. A first evolution of neural activity in the test subjects is then determined and compared with a second evolution of neural activity. This second evolution of neural activity is obtained from control subjects performing the sustained task in the absence of the test compound. The test compound is then designated to be a candidate drug when a difference between the first and second evolutions of neural activity is above a difference threshold.

11 Claims, 11 Drawing Sheets

SPATIAL EVOLUTION OF NEURAL ACTIVITY

PRIOR APPLICATIONS

This application claims the benefit of U.S. Provisional Patent Application entitled "SPATIAL EVOLUTION OF NEURAL ACTIVITY" Ser. No. 60/480,034 filed on Jun. 20, 2003.

FIELD OF INVENTION

The invention relates to the observation of the spatial evolution of neural activity, and in particular, to the use of such observations for development of drugs for treating neurological disorders.

BACKGROUND

The process of discovering new drugs for treatment of medical disorders often requires administering hundreds of test compounds to human volunteers. If the test compound relieves the manifestations of the disorder, it is considered to be a candidate drug and subjected to further testing.

For many disorders, the manifestations of the disorder are readily observable. However, in the case of neurological disorders, the manifestations are more difficult to quantify. For example, if one were to give a test compound to a volunteer afflicted with Alzheimer's, one would want to test the effect on that volunteer's short term memory. Each such test is a time-consuming proposition. Adding to this difficulty is the need to test enough volunteers to ensure that the conclusions drawn from these tests merit statistical significance.

Other neurological disorders, for example epilepsy, are characterized by transient episodes. The search for drugs having therapeutic value in treatment of epilepsy thus requires long periods of time during which one must somehow monitor the frequency, duration, and severity of seizures. The search for drugs effective in suppressing symptoms of schizophrenia requires somehow determining the extent to which a volunteer's perception of reality differs from reality, a measure that is fraught with subjective uncertainties.

SUMMARY

The invention is based in part, on the recognition that the spatial evolution of neural activity provides insight into the potential effectiveness of a test compound at treating a particular neural disorder. This avoids the difficulties associated with observing gross behavioral manifestations of the disorder.

In one aspect, the invention includes a method for identifying a candidate drug. The method includes administering a test compound to test subjects and having the test subjects perform a sustained task. A first evolution of neural activity in the test subjects is then determined and compared with a second evolution of neural activity. This second evolution of neural activity is obtained from control subjects performing the sustained task in the absence of the test compound. The test compound is then designated to be a candidate drug when a difference between the first and second evolutions of neural activity is above a difference threshold.

In one practice of the invention, the test subjects are selected from among those afflicted with a neurological disorder for which the candidate drug is intended to have therapeutic value, and the control subjects are selected from among those that are free of the disorder, Exemplary disorders include Alzheimer's disease, Parkinson's disease, and schizophrenia.

A variety of sustained tasks can be performed, depending on the type of neural activity that is to be observed. For example, the sustained task can be a cognitive task, an N-back task, a semantic reasoning task, or a visuospatial recognition task.

A variety of imaging methods can be used. For example, in one practice of the invention, determining a first evolution of neural activity includes obtaining a sequence of magnetic resonance images of each of the test subjects during performance of the sustained task.

In another practice of the invention, determining a first evolution of neural activity includes collecting task data indicative of evolution of neural activity during performance of the sustained task. The task data is then filtered to remove contributions arising from background neural activity.

In some practices of the invention, the background neural activity includes neural activity associated with performance of a reference task. However, in other practices, the background neural activity includes neural activity associated with a selected portion of the test subject. In particular, the background activity can be associated with the selected portion during performance of the sustained task.

Alternatively, determining a first evolution of neural activity can include having the subjects perform the sustained task during a first plurality of task intervals, each having at least a first time segment and a second time segment. Data from the first and second time segments is then collected into respective first and second data sets. These data sets are then filtered to remove a contribution arising from background neural activity. Such filtering can be performed by, for example, performing a correlation between data representative of the background neural activity and the first and second data sets, or performing a t-test between data representative of the background neural activity and the first and second data sets.

In another aspect, the invention includes a method for evaluating an effect of a physiologic stimulus on treatment of a neurological disorder, This method includes comparing evolution of neural activity between first and second groups, with the subjects in the first group having been administered the stimulus and the subjects in the second group not having been administered the stimulus. On the basis of a difference between the evolution of neural activity, an efficacy of the stimulus is determined.

Certain practices include the additional step of selecting the stimulus to be a pharmacological agent.

Other practices include those in which comparing evolution of neural activity includes obtaining functional MRI data for subjects in the first and second groups.

In some practices, comparing evolution includes having subjects from the first and second groups perform a sustained task.

In other practices, comparing evolution comprises having subjects from the first and second groups alternate between performing a sustained task and not performing the sustained task.

The invention also includes systems having an imaging system and a data processing system configured to carry out the method recited above.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
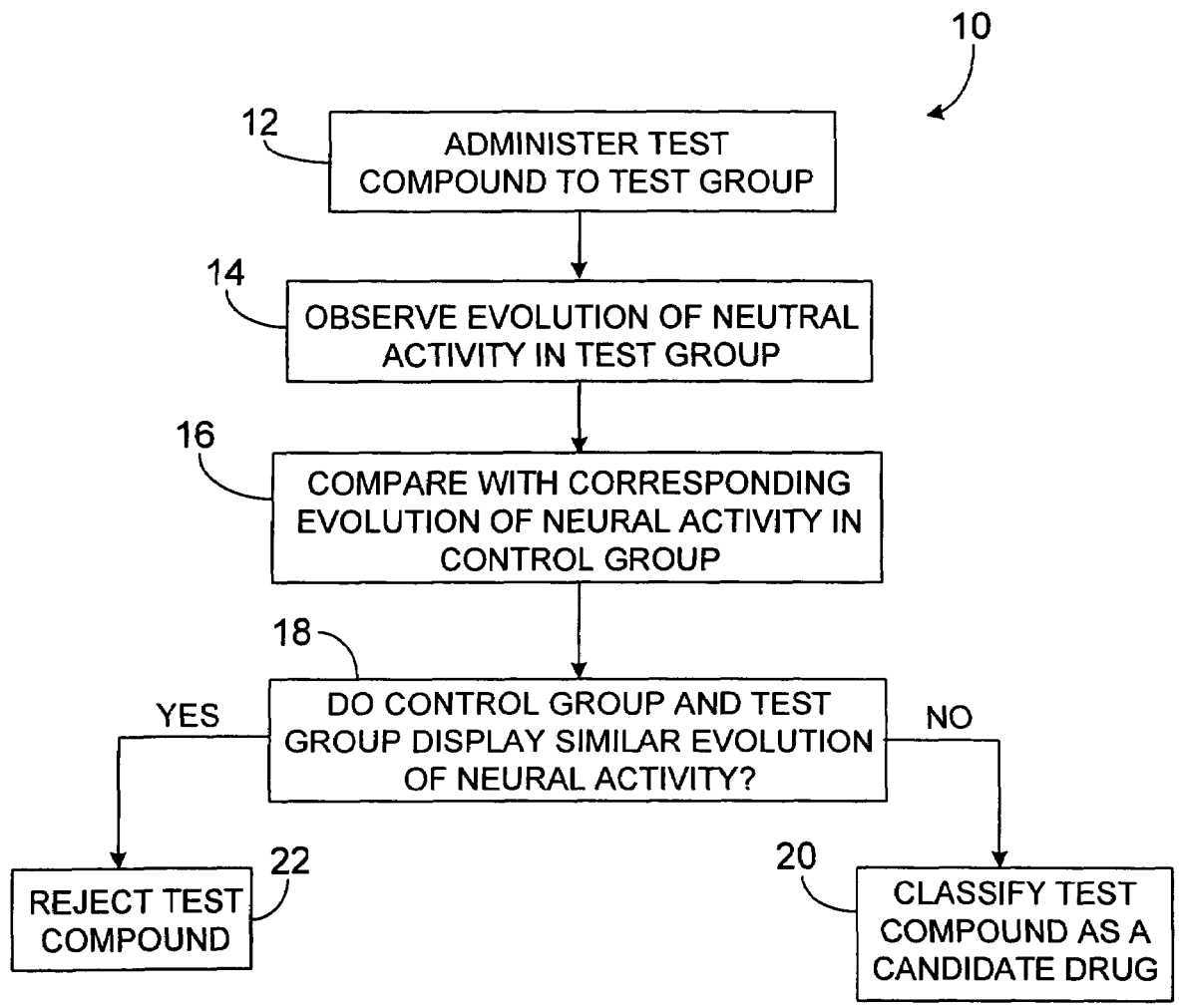
FIG. 1 is a flow chart of a drug screening method.

Referring to FIG. 1, a new method 10 for identifying a candidate drug for treatment of a neurological disorder depends in part on administering a test compound (step 12) to a test group of test subjects afflicted with the disorder and visualizing the evolution of neural activity in those subjects (step 14). This evolution of neural activity is then compared with the corresponding evolution of neural activity as observed in a control group of healthy subjects who are free of the disorder (step 16). To the extent that the evolution of neural activity observed in the test group differs from that observed in the control group (step 18), the test compound is considered to be a candidate drug for treatment of that disorder (step 20). If the evolution of neural activity observed in the control group is similar to that observed in the test group, the test compound is removed from further consideration as a candidate drug (step 22).

Figure 2:
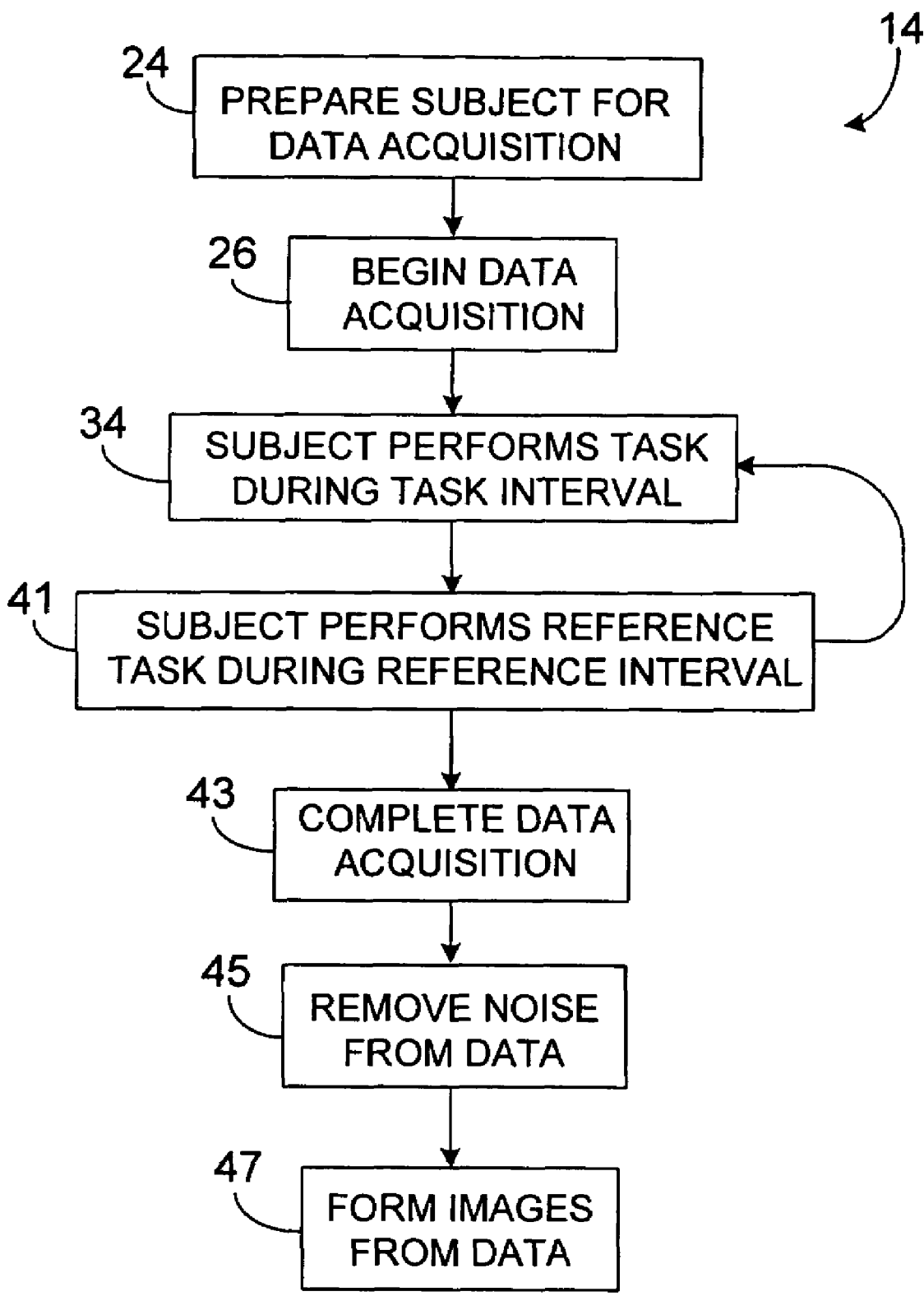
FIG. 2 is a flow chart of the process for observing the evolution of neural activity in FIG. 1.

As shown in FIG. 2, observing the evolution of neural activity (step 14) in a test subject begins with the preparation of a portion of the subject for acquisition of sequential images (step 24). Because of the volume of neural activity that takes place within it, the brain, or a portion thereof, is a natural choice for observation of neural activity. However, the method disclosed herein is applicable to observation of neural activity in any type of neural tissue.

Imaging can be accomplished by a variety of image acquisition systems, for example, MRI ("magnetic resonance imaging") systems, PET ("positron emission tomography") scanners, quantitative electro-encephalography ("QEEG") or magneto-encephalography ("QMEG") systems. Thus, preparation for imaging can include having the subject's head enter the field of an MRI machine, injecting a radioactive tracer into the subject and appropriately positioning the subject within a PET scanner, or attaching electrodes and/or pick-up coils to appropriate areas of the subject's scalp.

Because of the difference between the paramagnetic properties of oxygenated blood and deoxygenated blood, MRI systems are particularly useful for image acquisition. The acquisition of multiple MRI images of the same region separated in time is often referred to as "functional MRI" or "fMRI."

Figure 3:
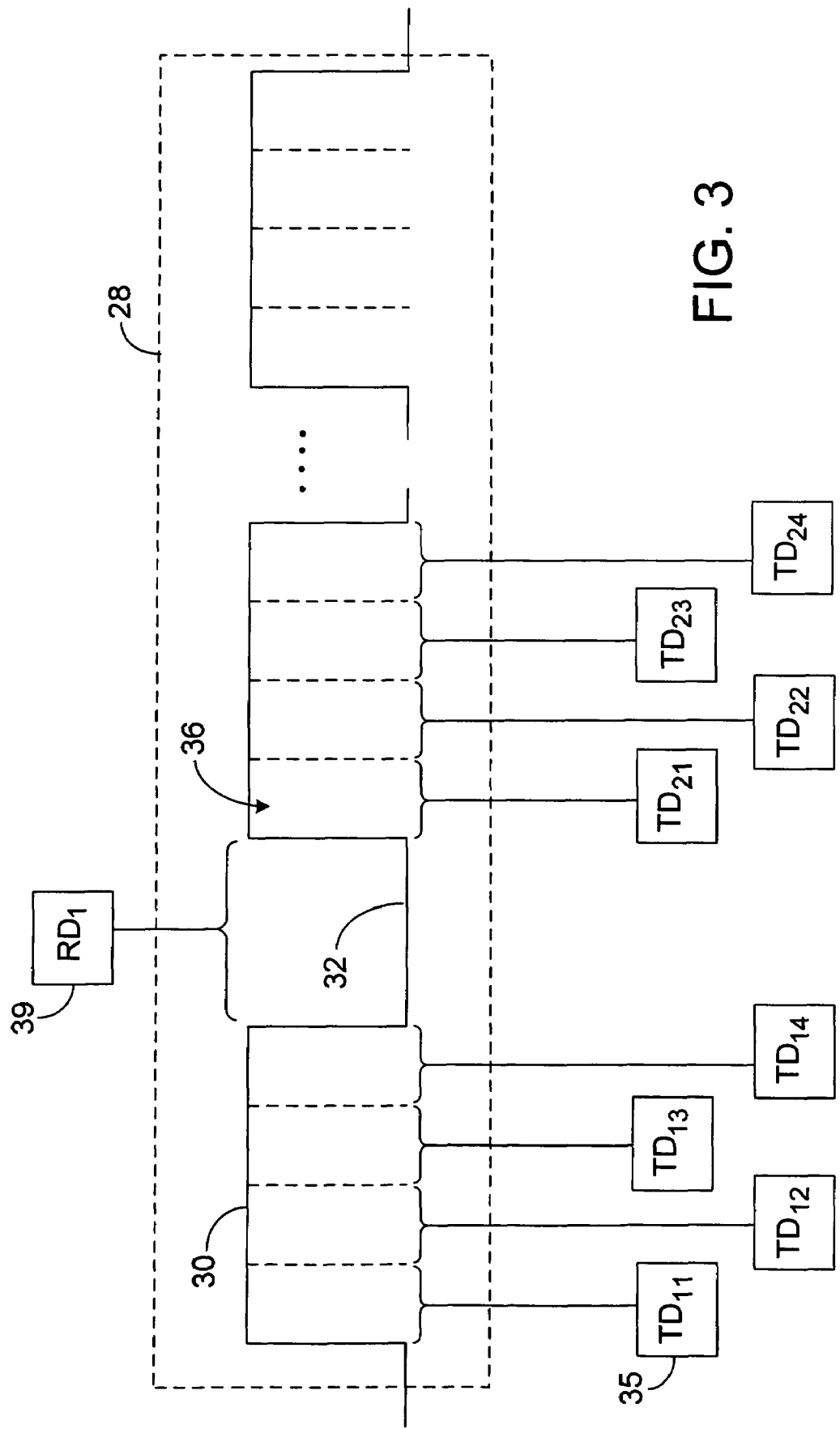
FIG. 3 is a diagram showing task intervals and resting intervals in a testing period.

Once the subject is prepared, the image acquisition system begins acquiring a sequence of data sets during a testing period (step 26). As shown in FIG. 3, a testing period 28 is divided into one or more task intervals 30 separated from each other by reference intervals 32. Although the task intervals 30 in FIG. 3 are shown as being the same length as the reference intervals 32, this need not be the case.

Referring again to FIG. 2, during the task intervals 30, the subject is asked to perform a task (step 34). Depending on the nature of the disorder and the portion of the brain in which neural activity is to be stimulated, the task can be a motor task, or any of a variety of cognitive tasks. For example, if the disorder is one that affects short-term memory, such as Alzheimer's disease, the task would be one that is expected to exercise that memory. An example of such a task is the 2-back test in which a subject is presented with a stream of symbols and asked to determine whether a current symbol matches the symbol that preceded the preceding symbol. For disorders of the visuospatial processing system, the test subject is asked to perform tasks that test the recognition of symbols or the identification of missing symbols from a set of symbols. For disorders of the brain's semantic processing system, the test subject is asked to perform simple reasoning tasks such as recognizing a presented word, retrieving from memory an association between that word and a category, and performing a function indicative of recognition of such an association.

Referring again to FIG. 3, each task interval 30 is divided into a number of time segments 36A-D. During each time segment 36A-D, the image acquisition system collects a task data set 35 $TD_{ij}$, where the index i refers to the task interval 30 and the index j identifies the time segment 36A-D within the task interval 30. Task data sets $TD_{1j}$, $TD_{2j}$, . . . $TD_{Nj}$, from corresponding time segments will later be combined to form one image that shows neural activity during a selected time interval following initiation of the task. For example, each task interval 30 will have a first time segment 36A, a second time segment 36B, and a last time segment 36D.

Figure 4:
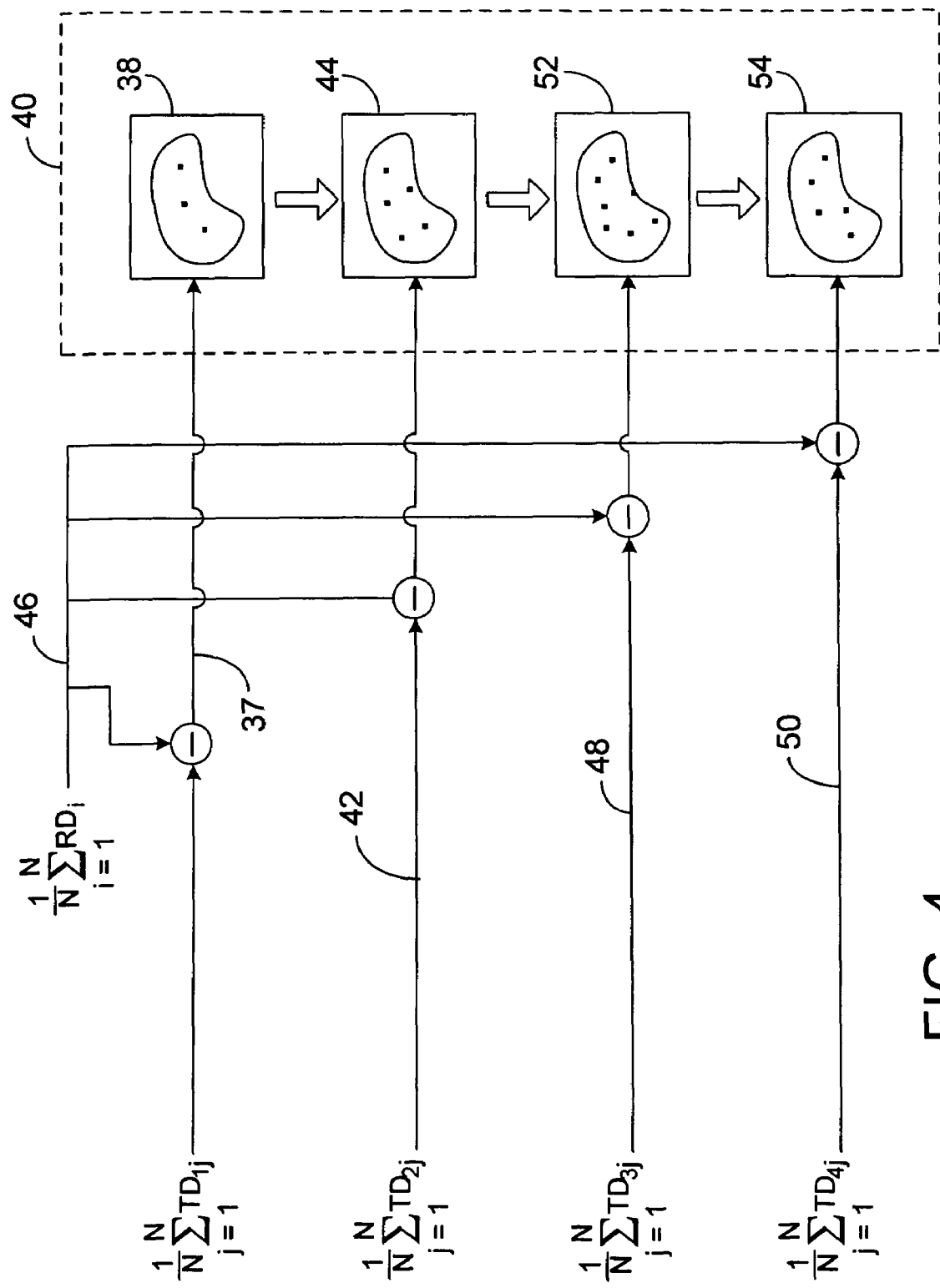
FIG. 4 is a signal-flow diagram showing statistical operations carried out on the data collected through the method shown in FIG. 2.

As shown in FIG. 4, the task data sets $TD_{1j}$ for first time segments of each task interval 30 will be averaged together, with the resulting time segment average 37 to be used in constructing a first image 38 in the sequence of images 40. Task data sets $TD_{2j}$ for second time segments of each task interval 30 will likewise be averaged together, with the resulting time segment average 42 being used in constructing the next image 44 in the sequence of images 40.

As the number of time segments 36 per task interval 30 increases, the temporal resolution with which the evolution of neural activity can be viewed also increases. On the other hand, as the number of time segments 36 increases, each time segment 36 becomes proportionately shorter. Hence the amount of data that can be gathered during any one time segment 36 decreases. It will therefore be necessary to have more task intervals 30, and hence a longer test period 28, to maintain the overall quality of the resulting images.

While the test subject performs the selected task, a great deal of background neural activity that is not associated with performance of that task continues to take place. Since it is only the neural activity associated with performance of the task that is ultimately of interest, it is desirable to filter out as much non-task related neural activity as possible.

Referring again to FIG. 3, reference data sets 39 ($RD_i$) acquired during reference intervals 32 provide a basis for filtering non-task related neural activity. Since the task is not being performed during the reference intervals 32, neural activity during the reference interval 32 provides an indication of background neural activity whose statistical effects on task data sets 35 can later be removed. Because the reference data set 39 is intended to represent constant background neural activity, there is no advantage to dividing the reference interval 32 into time segments and collecting reference data sets 39 in each such time segment. Consequently, there is generally only one reference data set 39 per reference interval 32. During the reference interval 32, the subject is asked to perform a reference task (see FIG. 2, step 41). This process is repeated, with the subject performing tasks during the task interval (step 34) and performing a reference task (step 41) during the reference interval 32, until the completion of data acquisition (step 43). The remaining steps in the new method are to remove the noise from the data (step 45) and to form images therefrom (step 47).

Referring again to FIG. 4, the reference data sets 39 are likewise averaged together. The resulting reference average 46 is statistically combined with each of the four time segment averages 37, 42, 48, 50 to extract only that data that represents neurological activity associated with performing the task. A variety of known statistical techniques are available for achieving this result. For example, one can perform a cross-correlation or T-test between the time segment averages and the reference average. Or, one can perform multiple regression analysis or any one of a variety of non-parametric statistical procedures to achieve this same goal. In addition, for each image 38, 44, 52, 54 in the image sequence 40, one might simply evaluate differences between the reference average 46 and the time segment average 37, 42, 48, 50 for that image 38, 44, 52, 54.

Whichever statistical technique is used, the end result is to distinguish a signal due to task-related activity from a reference signal that, in this case, corresponds to background activity. However, there is no requirement that the reference signal correspond to background activity. For example, in some cases, it may be desirable to identify portions of the brain whose neural activity is correlated with a reference portion of the brain. In such a case, the reference signal would be a measure of the time-varying neural activity within the reference portion of the brain.

In the case in which the reference signal corresponds to activity in a reference portion of the brain, the reference interval 32 is no longer necessary for collecting reference information. However the reference interval 32 may still be necessary to allow the test subject to rest, thereby allowing neural activity to die down so that the task can be always be repeated against the same backdrop of neural activity.

In this case, in which the image sequence 40 shows neural activity that corresponds to neural activity in a reference portion of the brain, both reference data sets 39 and task data sets 35 are collected during performance of the task, i.e. during the task interval 36. Data arising from the reference portion of the brain is sequestered from data arising from the remainder of the brain and processed as described above in connection with processing the task data sets 35. In effect, the only distinction is that the reference data set 39 no longer represents the generally constant background neural activity present when the test subject is not performing a task. Instead, the reference data set 39 now represents the time-varying neural activity of a selected portion of the brain during performance of the task. The distinction is thus analogous to the difference between determining the trajectory of a moving target relative to a stationary background and determining the trajectory of a moving target relative to a moving object.

The procedures set forth above are also applicable to the collection of data indicative of evolution of neural activity in healthy subjects from whom the test compound is withheld. Such data, collected in the manner set forth above, can be used as a basis for comparison to determine whether a particular test compound is effective.

Observation of the spatial evolution of neural activity as discussed above has applications other than screening drugs. For example, such observations may assist in diagnosing a disorder or, in the case of patients already known to have the disorder, monitoring the disorder. For patients already being treated for a disorder, such observations can be used to monitor the effectiveness of the treatment. In addition, the methods described herein can also be used to identify suitable test subjects for drug screening studies.

EXAMPLES

The invention is further described in the following examples, which do not limit the scope of the invention described in the claims.

In the following examples, various tasks are performed by test subjects and the resulting spatial evolution of neural activity is shown. The choice of task is selected on the basis of the neural disorder for which a drug is sought.

Example 1

Working Memory Task

In an N-back task, a subject is shown a string of letters, one letter at a time. The subject must recall whether a currently presented letter matches the Nth preceding letter. The N-back test has been used extensively to stimulate areas of the brain during acquisition of functional MRI images. In particular, the N-back test is known to stimulate bilateral dorsolateral prefrontal, dorsolateral parietal, and medial frontal cortical activity. Such tests are discussed in Braver, et al. "A Parametric Study of Prefrontal Cortex Involvement in Human Working Memory," Neuroimage 1997, 5:49-62. However, such tests do not show the evolution of neural activity over time while performing the N-back task. While these tests may show what portions of the brain were used at some time during the N-back task, they do not show when those portions were used, how long those portions were used for, and what portions were being used at the same time. As a result, these tests do not indicate whether portions of the brain that engage in neural activity during the N-back task change over time by, for example, growing or shrinking. These tests also fail to show whether, in the course of performing the N-back task, additional portions of the brain are recruited to assist with the processing demands.

In an effort to identify spatial evolution of neural activity during a 2-back task, seventeen healthy adults aged 20-62 with a mean age of 35 were recruited as test subjects. Ten test subjects were female, and sixteen were right-handed. No test compound was administered to the test subjects. Nevertheless, the procedure described herein demonstrates the feasibility of forming sequential images indicative of the evolution of neural activity in response to a sustained task.

In this example, the image acquisition system was a 1.5 Tesla GE Sigma LX MRI system capable of whole brain echo-planar functional imaging using a GRE ("Gradient Recall Echo") sequence in which the relaxation time, TR, was 3 seconds, the echo time was 60 milliseconds, the flip angle was 90 degrees, the slices were 5 millimeters thick, the field of view ("FOV") was 24 centimeters, and the matrix was a 64×64 matrix. For high-resolution whole brain anatomic imaging, an SPGR ("SPoiled Gradient Recalled") sequence was used in which the relaxation time was 22 milliseconds, the FOV was again 24 centimeters, and the matrix was a 256×256 matrix.

The test period began with a 27-second reference interval 32 followed by the first of eight task intervals 30, each 36 seconds long. Seven 27-second reference intervals 32 separated each task interval 30 from its preceding task interval. During the task intervals 30, the test subjects performed a 2-back task. In the 2-back task, the subjects were shown a sequence of letters one at a time and asked to determine whether the currently presented letter matched the letter that preceded the preceding letter. The subject would press one of two buttons depending on whether or not this was the case. During the reference intervals 32, the subject was asked whether the presented letter matched a predetermined target letter. Again, the subject would press one of two buttons depending on whether or not this was the case.

Preprocessing steps included motion correction, temporal smoothing, 3 millimeter spatial blurring, and standardization in Talairach space using AFNI software, as described in Cox, "AFNI software for the analysis and visualization of functional magnetic resonance neuroimages," Compt. Biomed. Res., 1996, 29:129-173.

Each 36-second task interval 30 was divided into four time segments, each of which lasted 9 seconds. For each subject, a task data set was acquired for each time segment 36. Task data sets for corresponding time segments in each of the eight task intervals 30 were then averaged together. From each of the resulting task averages, average reference data obtained during the reference interval 32 was subtracted. The resulting eight differences were compared to a hypothetical mean of zero using a one-sample t-test. The resulting individual "t-maps," or maps of voxel intensity, were averaged to give four group summary t-maps, one for each of the four time segments. The number of significantly active voxels (i.e. those for which $p<0.001$, where p is the probability that the voxel is not significant) within anterior/frontal and posterior/parietal brain regions of interest were tallied from this data.

Next, a repeated measures ANOVA (ANalysis Of VAriance) was conducted using the averaged difference scores for each time segment as the dependent variable. This identified voxels that changed during a particular time segment. The relaxation times, TR, were then randomized and the foregoing statistical procedures were repeated to identify false positive rates and to determine significance thresholds. With a threshold $p=0.001$, no voxels were active in the randomized data.

Figure 5:
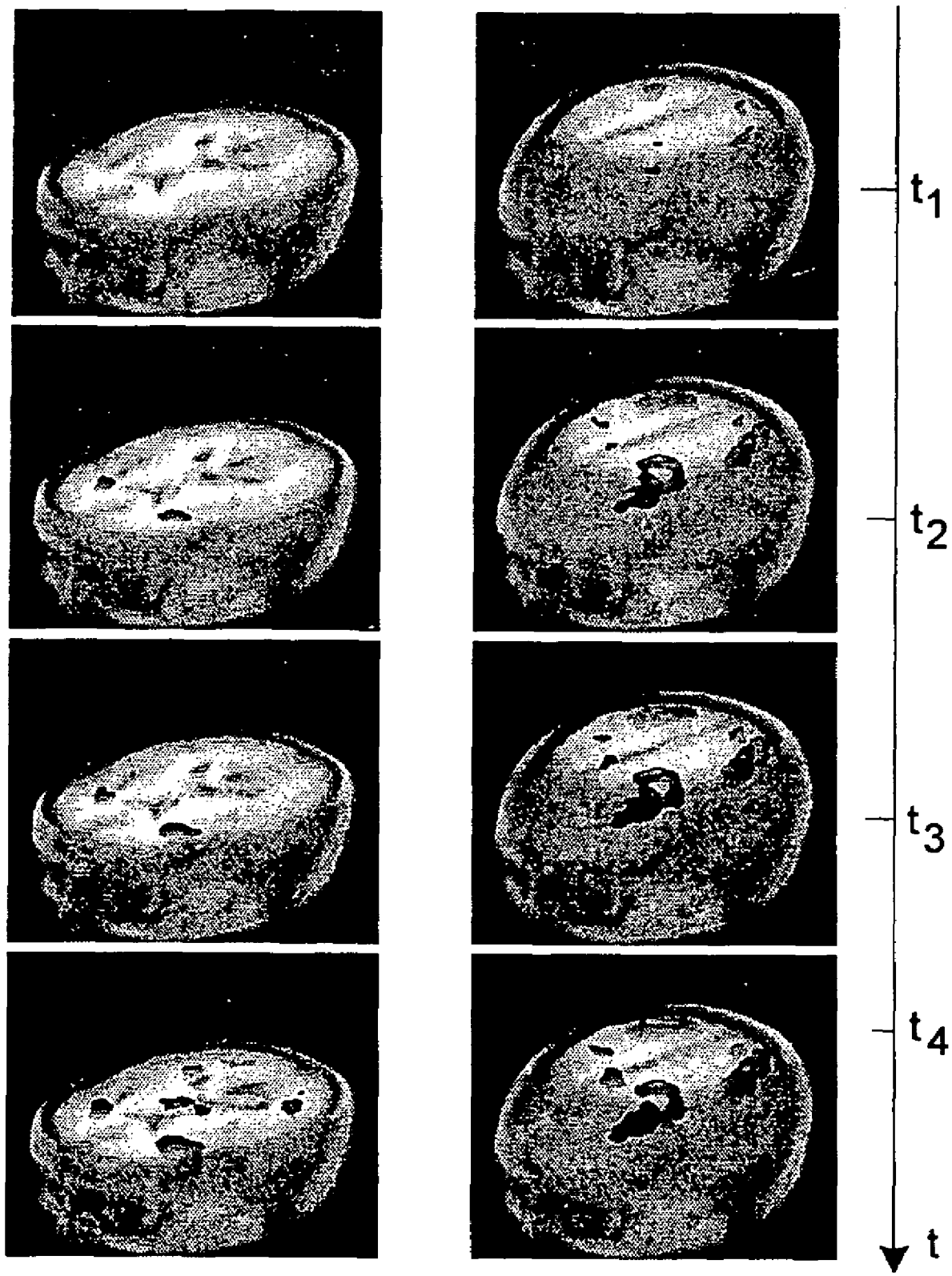
FIG. 5 is a set of MRI scans showing temporal evolution of neural activity while the subject is performing a working-memory task.

The resulting MRI images are shown in FIG. 5. The first column of four images shows a transverse cut at each of the four different 9-second time segments. The second column of four images shows another view of the brain in those same four time segments. It is apparent from FIG. 5 that as a test subject performs a verbal working memory task, active portions of the brain somehow recruit additional portions for assistance. By the fourth time segment, neural activity has spread from the initial centers of neural activity shown in the first time segment. This occurs even though the task demand itself is constant. By way of analogy, it is as if one were to suspend a weight with one's right arm, and after a few minutes, muscles in one's left arm or a leg could somehow be recruited to assist the right arm in suspending that constant weight.

Figure 6:
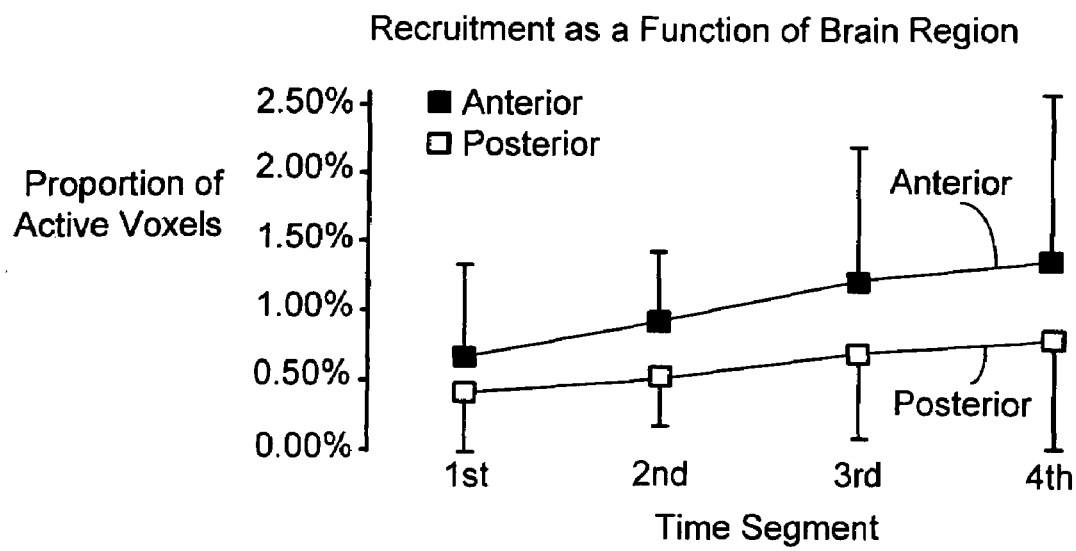
FIG. 6 is a graph showing the extent of voxel recruitment in anterior and posterior regions of the brain during performance of a working-memory task.

FIG. 6 shows the percentage of active voxels, i.e. those exhibiting significant neural activity, for each of the four 9-second time segments. As shown in FIG. 6, it was only the anterior region of the brain that exhibited a significant increase in the number of voxels over time, whereas the posterior region exhibited only a trend toward significance.

Figure 7:
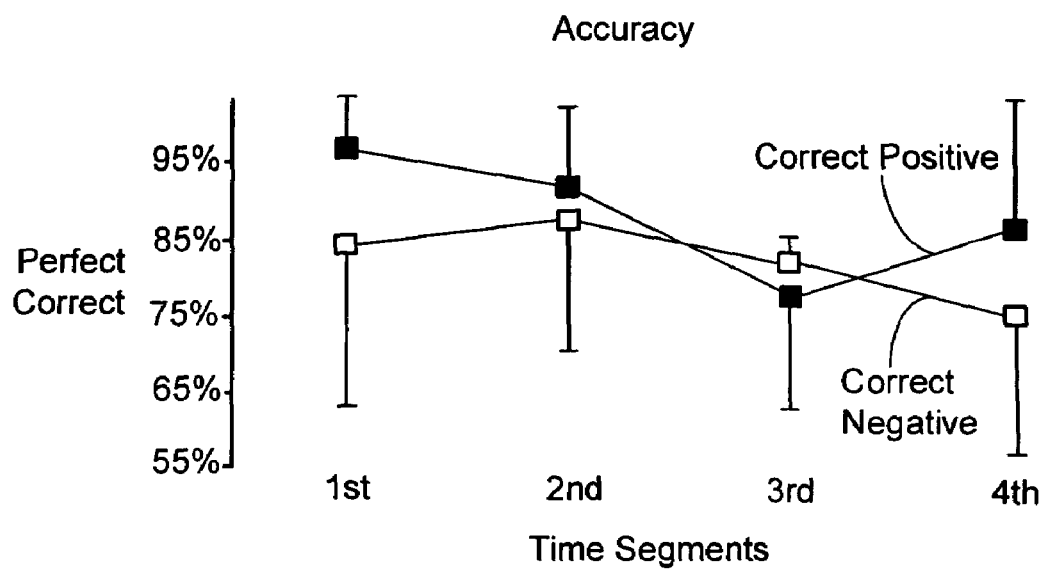
FIG. 7 is a graph showing the evolution of working-memory performance over time.

FIG. 7 shows the percentage of correct answers entered by the test subjects in each of the four time segments during which they were performing the working-memory task. A comparison of FIGS. 6 and 7 suggests that the performance of the test subjects was inversely related to the extent of recruitment. This may reflect compensation for impaired temporal information flow to frontal decision making areas, short-term memory buffer saturation in the parietal regions, or both. Recruitment may have arisen because the short term memory buffer may have been unable to efficiently cycle through constantly changing incoming information, thereby forcing it to recruit additional parietal resources. In particular, frontal systems, such as the frontal lobes and the medial thalamus, attempt to manage this information load more effectively by recruiting disproportionately more brain resources. This may reflect a previously unknown temporally-mediated capacity constraint on a neural network performing a sustained N-back working memory task. The time-segment analysis method disclosed herein can be used to demonstrate evolution of neural activity in the brain during other sustained tasks.

Example 2

Simple Motor Task

In a second example, MRI was acquired with a 1.5 T GE Signa-LX scanner (GE Medical Systems, Milwaukee, Wis.) using a standard RF quadrature head volume (birdcage) coil. High-resolution [(256 (256, 24 cm (24 cm), 1.5 mm slice thickness], T1-weighted sagittal plane images were acquired with a spoiled GRASS sequence (TR/TE=22/5 milliseconds, $\theta=22$ degrees, NEX=1) for anatomic localization of functional activation. Data was acquired during runs of the functional tasks using a GRE-EPI sequence (TR/TE=3000/60 msec, $\theta=90$ degrees) with contiguous axial slices positioned to cover the entire brain volume [(64×64, 24 cm×24 cm), 5 mm slice thickness, generally 25-28 slices]. All task instructions and stimuli were presented to the subjects visually by back-projecting information on a screen placed at the foot of the scanning table. Subjects were able to view the screen using a mirror built into the RF head coil positioned above their eyes and angled out from the bore of the magnet.

Test subjects were all healthy, normal, right-hand dominant adults aged 20-62 (mean=36). Not all experiment paradigms were administered to all subjects.

During the simple motor function task, subjects were instructed to repetitively open and close their right hand at a self-paced, consistent rate over a 45-sec period. The opening/closing activity was alternated with a 45-sec rest phase in a four-cycle blocked-paradigm over a six-minute period (i.e., 120 repetitions of the 3-sec TR GRE-EPI acquisition). Subjects repeated two runs of this task and the data was concatenated to produce one contiguous dataset for analysis.

All fMRI data were analyzed using AFNI as discussed above in connection with Example 1. For each subject, time-series images were spatially registered to minimize effects of head motion. The two individual runs of each 4-cycle task were concatenated to produce a single dataset of 240 repetitions. With the concatenated dataset, cross-correlation analysis was performed against ideal waveforms created by dividing the stimulus epochs into subsets of TRs (MRI relaxation times) with each of the control epochs maintained whole. Correlation-coefficient maps obtained from each of the ideal waveforms were thresholded for statistical significance using a routine written to control the false discovery rate as discussed in Genovese C R, "Thresholding of statistical maps in functional neuroimaging using the false discovery rate," Neuroimage 15:870-878 (2002). The threshold applied to the simple motor function was at the 0.001 level and for the three other paradigms at the 0.01 level. Individual subject anatomical and functional images were then interpolated to volumes divided into one cubic millimeter voxels, co-registered, transformed to standard Talairach coordinate space as discussed in Talairach, et al., "Stereotactic Atlas of the Human Brain," Thieme Medical Publishers, New York, N.Y. (1988), and spatially smoothed using a 4-mm Gaussian FWHM ("Full Width at Half Maximum") filter.

To obtain information regarding the group response to a given stimulus paradigm, individual, spatially-normalized (i.e., transformed to Talairach coordinate space), subject correlation data sets were grouped by averaging their thresholded data sets, yielding averaged activation maps for each subset of the stimulus epoch. Since the information of interest was the location of spatial evolution of neural activation during a task interval, activity in the subject-averaged output was classified in a binary (on or off) manner.

Figure 8:
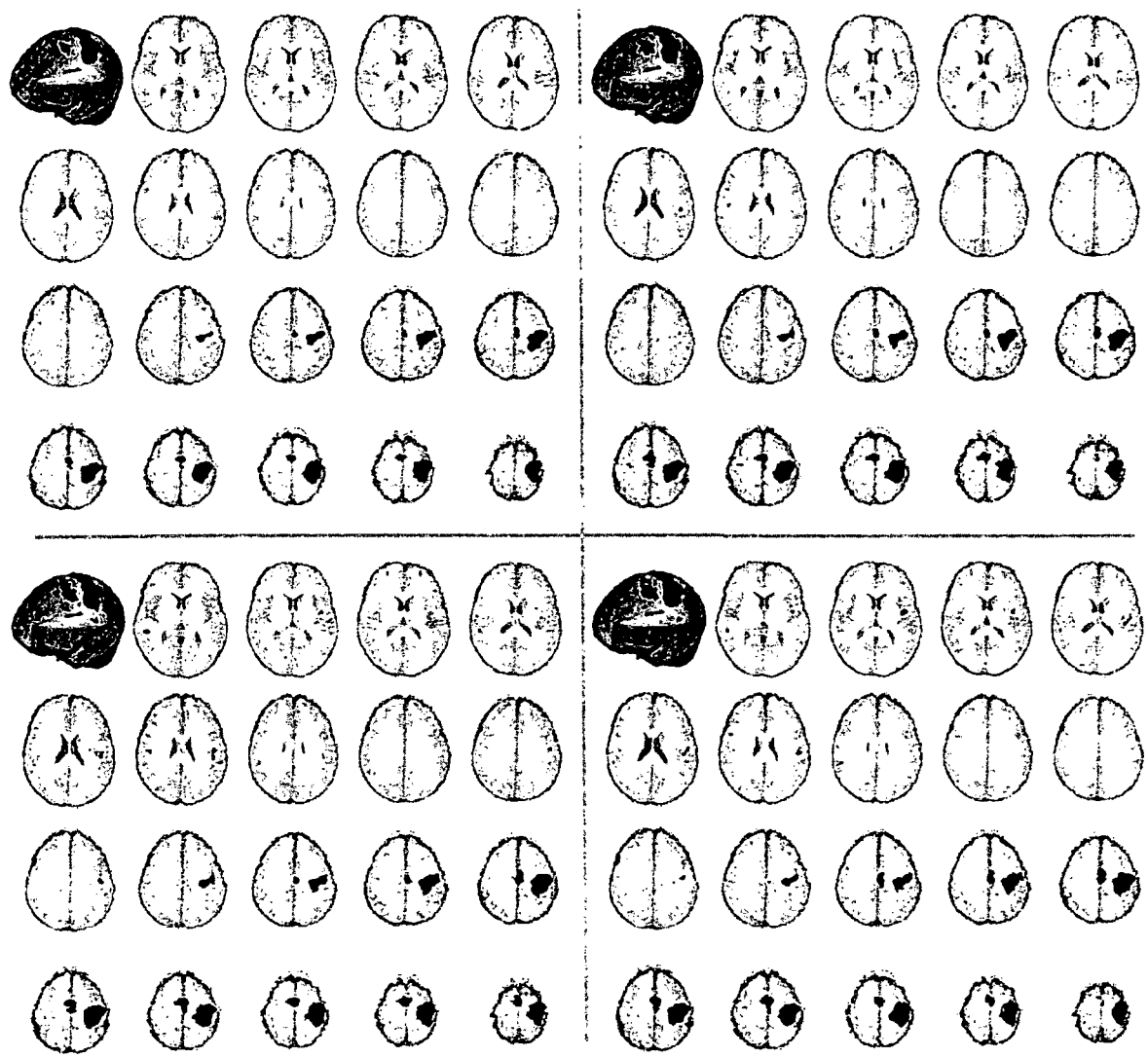
FIG. 8 is a set of MRI scans showing temporal evolution of neural activity while the subject is performing a simple motor task.

FIG. 8 shows the resulting images acquired during the four time segments. Each quadrant of images in FIG. 8 represents images acquired during one time segment. The first and last time segments are at the upper left and lower right respectively. The second and third time segments are at the lower left and upper right respectively. The images within one quadrant correspond to different transverse sections of the brain during that time segment.

The regions of activation in FIG. 8 represent the FDR thresholded (q=0.001) correlation output averaged from ten subjects, overlaid on the averages of their anatomical data. Axial plane images (3-mm offset between slices) and the corresponding volume renderings with cutouts positioned to highlight medial frontal and left hemisphere features of the activation output are provided from each of the four time interval segments. Activation during the first time segment is localized completely in the medial frontal and left hemisphere dorsolateral prefrontal cortex (DLPFC), areas consistent with initiation and execution of motor plans, respectively. During the subsequent time segments, activation in these two regions persists and remains relatively constant in volume. By the second time segment, spurious areas of bilateral activation in the inferior parietal lobes are observed. These spurious areas persisted and, in some cases, expanded over the course of the remaining time segments.

From this paradigm of self-paced, sustained motor activity, we observe patterns of neural activation that remain rather constant over the duration of the task and that are consistent with similar imaging studies of motor function, for example in Rao, et al. "Functional magnetic resonance imaging of complex human movements," Neurology 43:2311-2318 (1993). To determine whether a statistically significant difference in regionally localized volumes of activation were present over the course of the intervals, three region-of-interest masks were created to encompass (1) left hemisphere primary sensorimotor region, (2) medial frontal supplementary motor area (SMA), and (3) right hemisphere primary sensorimotor region. Masking individual subject activation maps from the four task intervals with the regions-of-interest enabled determination of the number of active voxels in a given region at each interval. A repeated measures ANOVA was conducted using the individual subject active voxel counts at each time segment as the dependent variable and found no significant variation in the volumes of activity over the course of the interval for any of the regions ($P>0.25$).

The results of this experiment add to the body of knowledge in the art by suggesting that the volume of neural tissue in the medial frontal region remains constant over the duration of a sustained motor task. Contrary to a previous study of the sensorimotor region discussed in Samuel, et al., "Exploring the temporal nature of hemodynamic responses of cortical motor areas using functional MRI," Neurology 51:1567-1575 (1998), the present experiment suggests the absence of any development of any substantial volume of activation in the contralateral primary motor region. The observation of activity in the inferior parietal lobe at the later time segments during the task is, however, consistent with other neuropsychological studies. The inferior parietal lobe is generally assumed to be involved in sensory awareness. This is based on the fact that neglect, which constitutes an attentional rather than a sensory deficit, is most commonly found after lesions of the inferior parietal lobe. This consistency supports the instructional constraints of the task where subjects were asked to perform the right-hand opening and closing at a self-paced, but consistent, rate.

Example 3

Visuospatial Processing

Data acquisition and data processing methods used in this example were the same as those used in Example 2. However, in this example, the task that the subjects were asked to perform was intended to stimulate neural activity associated with visuospatial processing.

Figure 9:
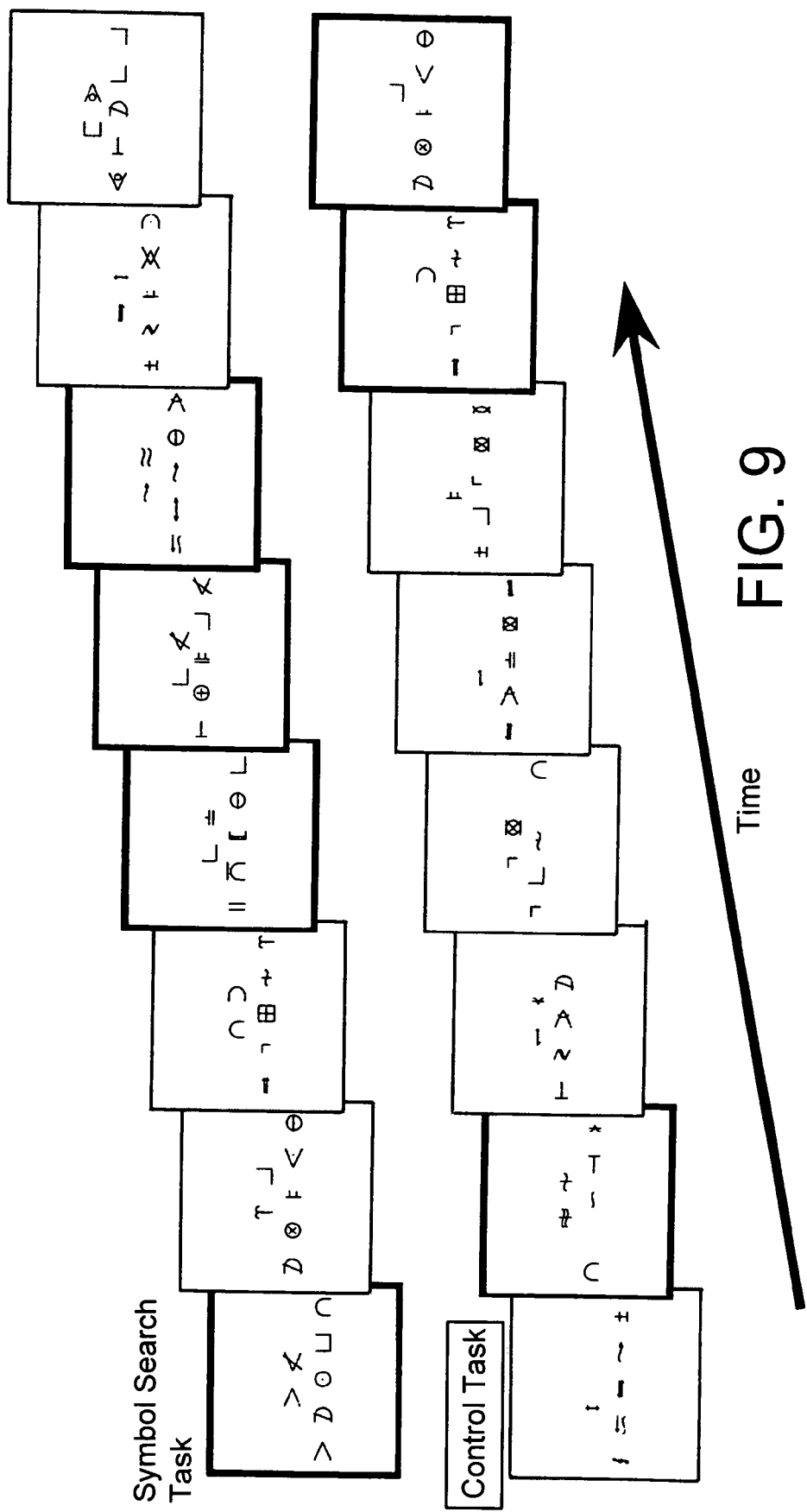
FIG. 9 is a diagram showing symbols used in a visuospatial processing task

The visuospatial task performed by the subjects was an adaptation of a widely used pencil-and-paper test of non-verbal intelligence: Wechsler Adult Intelligence Scale (WAIS-III). This task can be understood with reference to FIG. 9, which shows an exemplary sequence of slides used in this task During the reference intervals, a control task was performed. In it, a series of slides showing symbol groupings was presented to the subjects. Two symbol groups were arranged on each slide: the upper group was a row of two symbols; the lower group, beneath the upper group, was a row of five symbols. One symbol in either grouping was missing. On a two-button keypad, the subject would press the button corresponding to the side of the slide that had the missing symbol.

During the task intervals, a symbol-search task was performed. In it, a series of symbol groupings, arranged in the same manner as in the control task, was presented. However, in this case, either symbol from the top grouping was a target for a possible match in the bottom grouping. The subject Was instructed to indicate whether one of the target symbols from the top grouping was located in the bottom grouping. A left button press indicated a positive match and a right button press indicated no match.

Both the control task and the symbol-search tasks were self-paced by the subject over a period of 45 seconds. The tasks were alternately performed during 45-second intervals during four task intervals over a six-minute period (i.e., 120 repetitions of the 3-second TR GRE-EPI acquisition). Subjects repeated two runs of this task and the resulting data was concatenated to produce one contiguous dataset for analysis.

The adaptation of the WAIS-III test used in this experiment differed slightly from the standard test. In the standard test, the target symbols are located horizontally from the choice symbol group; whereas in the modified version used in the present experiment, the symbol groups were vertically offset from one another. This modification was not expected to have a significant effect on subject performance, as the geometry of the symbols was, in general, of sufficient complexity to enforce a memory component to the task.

Figure 10:
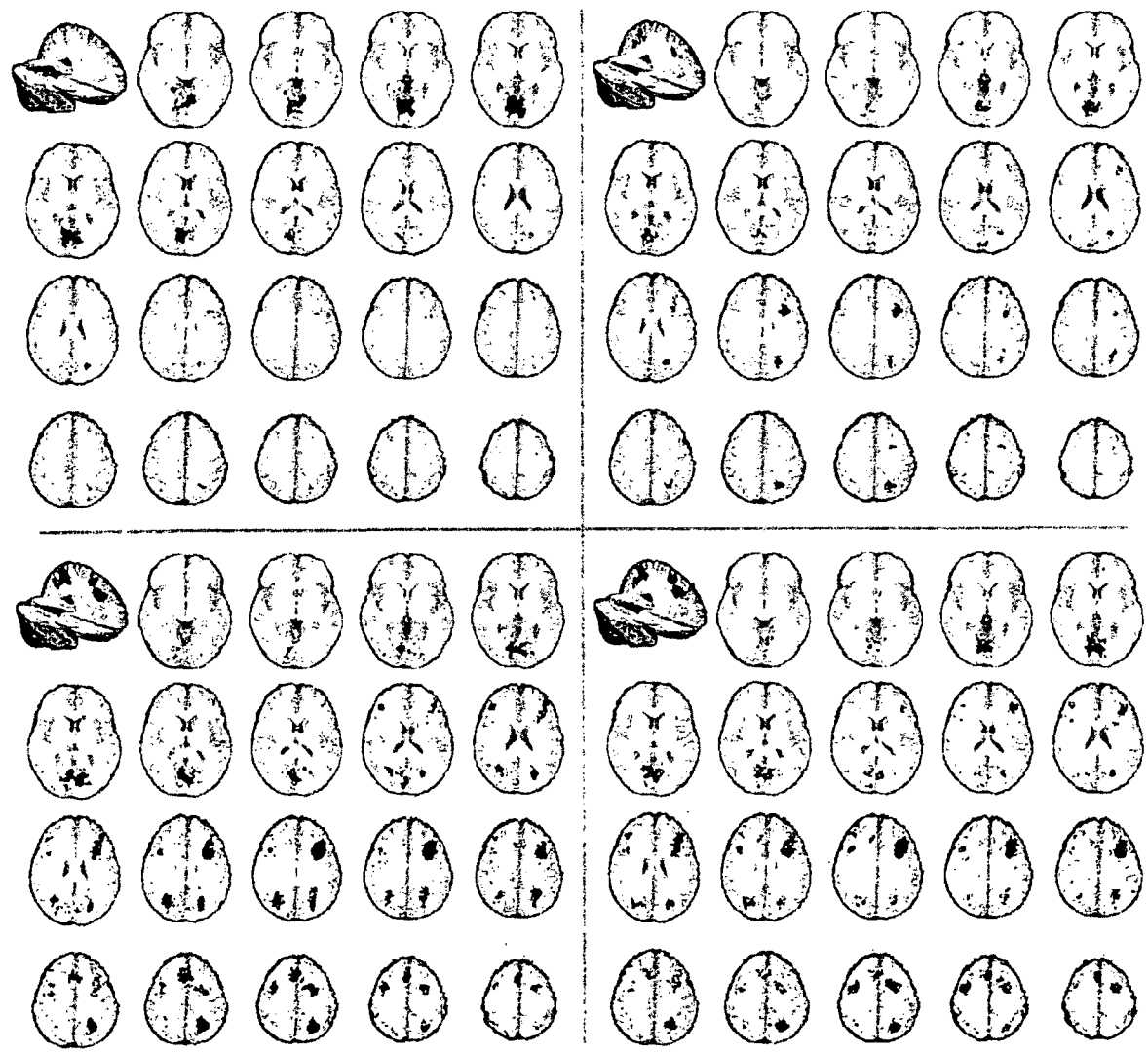
FIG. 10 is a set of MRI scans showing temporal evolution of neural activity while the subject is performing a visuospatial processing task.

FIG. 10 shows a sequence of magnetic resonance images obtained while the test subjects performed the visuospatial processing task. The layout of the images in FIG. 10 is as discussed above in connection with FIG. 8. These images show neural activation in areas consistent with the visual, working memory and decision-making requirements of the task. The regions of neural activation in this figure represent the FDR thresholded (q=0.01) correlation output averaged from nine subjects. Axial-plane images (3-mm offset between slices) and the corresponding volume renderings with cutouts positioned to highlight occipital lobe and left hemisphere regions of activation output were provided from each of the four time interval segments in sequential order.

A large volume of activation was noted in the occipital lobe region during the first time segment. Activation in this region dissipated over the time segments, but a core volume nevertheless remained through the later time segments. The core volume was located in areas consistent with primary visual processing. Regions of neural activation in the left-hemisphere inferior frontal and posterior parietal lobes were noted during the first time segment. These regions progressively increased in volume throughout the remaining time segments. By the third time segment, homologous regions in the right hemisphere appeared active. The neural activity in the inferior frontal and posterior parietal regions was consistent with, respectively, the executive control and iconic working memory demands of this task.

During the second time segment, neural activity in the left hemisphere DLPFC region became apparent. By the third time segment, the neural activity in this region had expanded. This expansion was concurrent with the onset of medial frontal and right hemisphere DLPFC activity. The regions into which expansion occurred were those known to be associated with the initiation and decision making aspects of the visuospatial processing task.

A prominent feature of the visuospatial processing activation in FIG. 10 was the variation in the volume of activation in the occipital lobe over the four time segments. The initial blush of activation at the first time segment is likely to have been a result of the inclusion of visual-feature-detection regions that extend beyond the primary visual cortex. This hypothesis is consistent with the notion that after the transition from the control task, the feature-detection areas of the visual cortex are re-engaged, thereby triggering neural activity beyond the primary visual cortex and into the secondary visual processing areas. As the symbol-search component of the task progresses, the regions required for feature-detection habituated and were no longer needed. In addition to the large occipital region of activity, the posterior parietal and bilateral frontal lobe regions, each respectively responsible for iconic memory and executive control functions, show evolving volumes of activity over the time segments, possibly reflecting a perceived increase in task difficulty over the duration of this task.

Example 4

Non-Stationary Noise

As noted above, there is always a certain amount of background neural activity in the brain. When we observed the spatial evolution of neural activity in the foregoing examples, we observed neural activity that differed from this background in a statistically significant manner. In the terminology of stochastic processes, this background represents stationary noise. Thus, in the foregoing examples, we observed the spatial evolution of neural activity against a backdrop of stationary noise.

It is also possible to observe the spatial evolution of neural activity against a background of non-stationary noise. For example, the neural activity in one portion of the brain can be viewed against the background of neural activity in another portion of the brain. Data derived from such observations can indicate whether or not those two portions of the brain are functionally linked.

Data acquisition and data processing methods used in this example were the same as those used in Example 1. The test subjects performed the same working-memory task discussed in Example 1.

Figure 11:
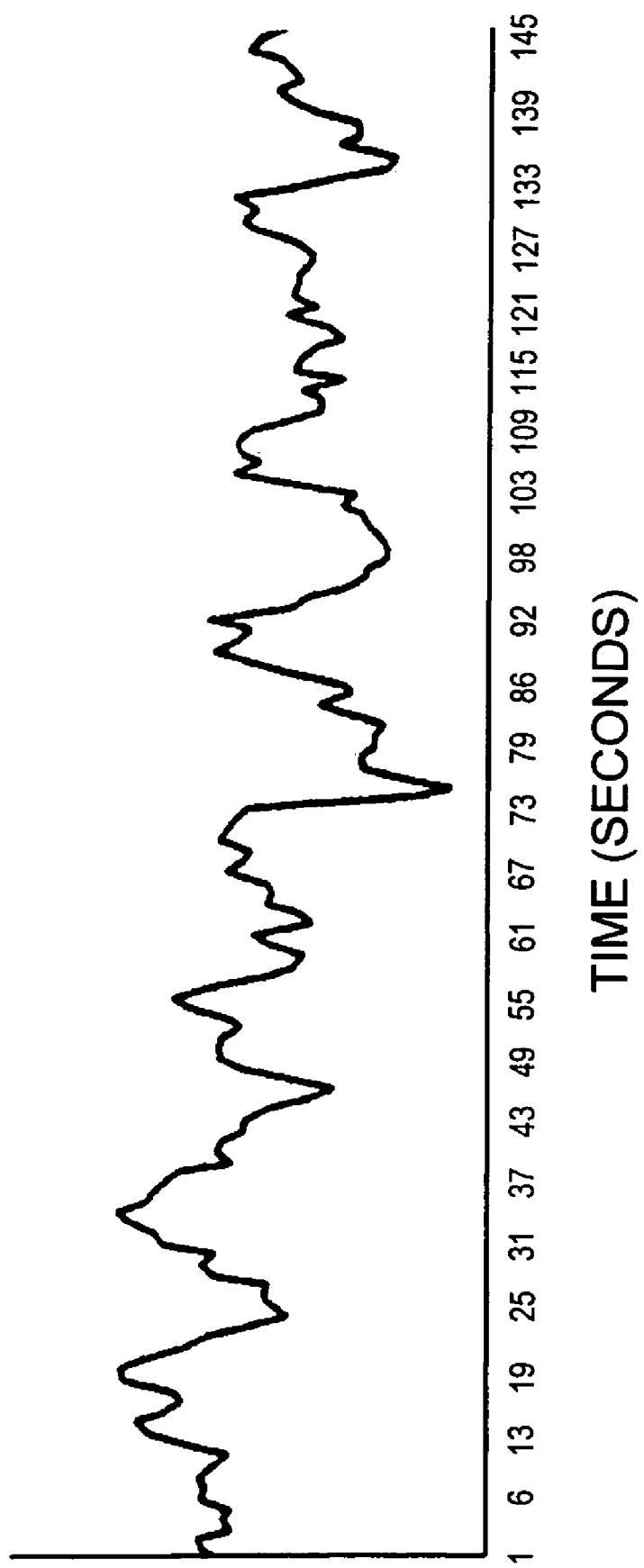
FIG. 11 is a graph representing neural activity in a portion of the thalamus.

In this example, the non-stationary noise was provided by the medial dorsal nucleus of the thalamus ("MDNt"). FIG. 11 shows a graph indicating the level of neural activity within the MDNt during the course of eight task intervals while the test subjects performed the N-back task as discussed in connection with Example 1. Data obtained from other portions of the brain was correlated with the data shown in FIG. 11. To the extent that neural activity in a portion of the brain exhibited time variation similar to that shown in FIG. 11, that portion of the brain could be considered functionally linked to the MDNt.

Figure 12:
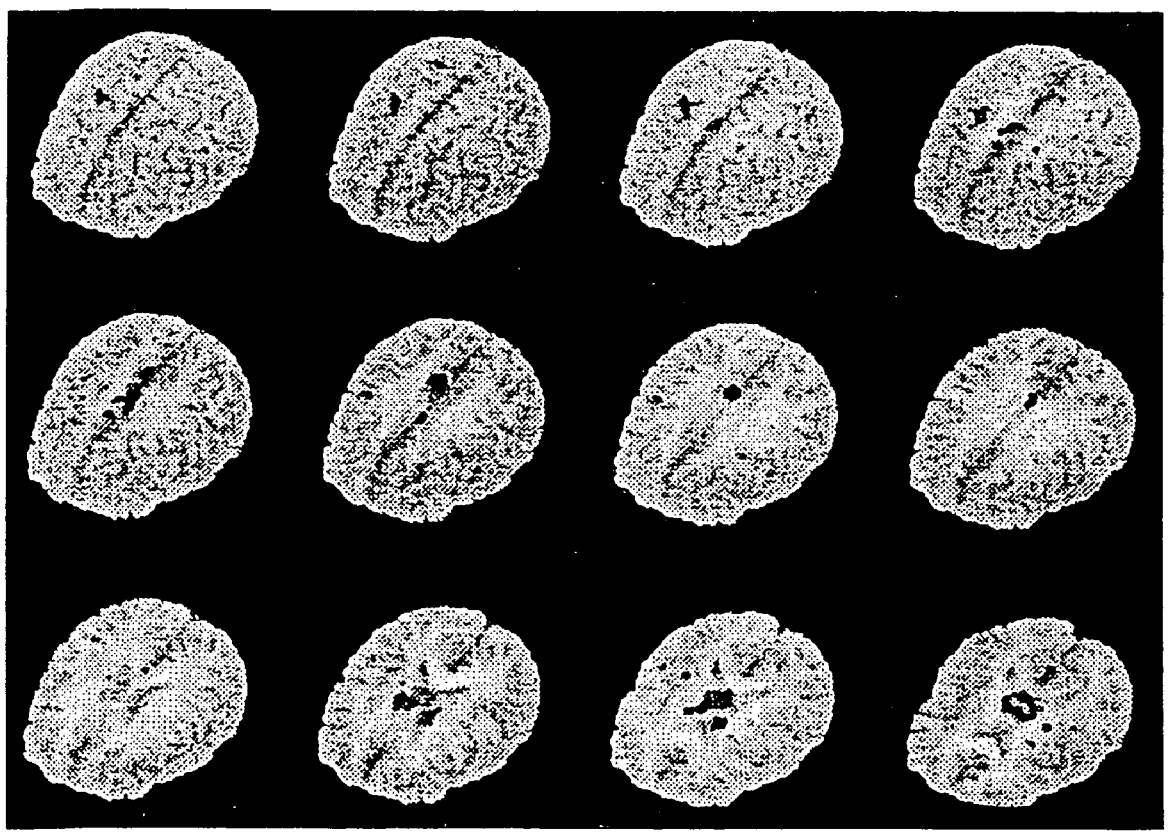
FIG. 12 is a graph showing three views of the brain during each of four time segments.

FIG. 12 shows three views of the brain during each of four time segments. The darkened portions of the brain represent those portions displaying neural activity correlated with the activity in the MDNt. FIG. 12 reveals bilateral caudate, cingulate/pericingulate/medial frontal cortical activity, and some bilateral dorsolateral prefrontal cortical activity. The 8-cycle waveform pattern that correlates these regions suggests that their neural activation is present throughout the task, but that this activation remains at a subthreshold level until the demands of the N-back task impose an additional metabolic load on these structures. Time-segment analysis and correlation methods such as that disclosed in this example are useful in demonstrating dynamic changes in other functionally related neural networks with different fMRI tasks.

SUMMARY

In these experiments, we demonstrated a new method for observing dynamic changes in the volumes of brain regions during a sustained task. The results of these experiments reinforce the hypothesis that brain regions adapt to the given task demands through either recruitment or discharge of adjacent areas of tissue. These results also indicate that traditional analysis of block-design fMRI studies may underestimate dynamic changes in brain regions during a sustained task.

The time-segment analysis method disclosed herein and demonstrated by the foregoing examples permit observation of region-specific variations in activation. From such observations, inferences may be made concerning how different brain regions adapt to and interact with one another during periods of extended activity. In addition, from such observations, inferences can be made concerning the therapeutic effectiveness of test compounds at a neurophysiologic level, thereby eliminating the need to rely on gross behavioral manifestations of neurological disorders.

The new methods set forth herein can be used to visualize evolution of neural activity in response to a sustained task by healthy test subjects, by test subjects afflicted with a disorder, or by test subjects afflicted with that disorder, before and/or after administration of a test compound. Accordingly, the procedures described herein can be used to identify candidate drugs from a set of test compounds in the manner discussed in connection with FIGS. 1 and 2.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a candidate drug for the treatment of Alzheimer's disease, the method comprising:
    administering a test compound to test subjects;
    having the test subjects perform a sustained N-back task;
    determining a first evolution of neural activity in the test subjects;
    comparing the first evolution of neural activity with a second evolution of neural activity, wherein the second evolution of neural activity is obtained from control subjects performing the sustained task in the absence of the test compound; and
    designating the test compound to be a candidate drug when a difference between the first and second evolutions of neural activity is above a difference threshold.

2. The method of claim 1, wherein the test subjects are selected from a population afflicted with Alzheimer's disease for which the candidate drug is intended to have therapeutic value, and the control subjects are free of the disorder.

3. The method of claim 1, wherein determining a first evolution of neural activity comprises obtaining a sequence of magnetic resonance images of each of the test subjects during performance of the sustained task.

4. The method of claim 1, wherein determining a first evolution of neural activity comprises:
    collecting task data indicative of evolution of neural activity during performance of the sustained task; and
    filtering, from the task data, a contribution to the task data arising from background neural activity.

5. The method of claim 4, wherein the background neural activity comprises neural activity associated with performance of a reference task.

6. The method of claim 4, wherein the background neural activity comprises neural activity associated with a selected portion of the test subject.

7. The method of claim 6, wherein the background neural activity comprises neural activity associated with the selected portion during performance of the sustained task.

8. The method of claim 1, wherein determining a first evolution of neural activity comprises:
    having the subjects perform the sustained N-back task during a first plurality of task intervals, each having at least a first time segment and a second time segment;
    collecting data from each of the first time segments into a first data set;
    collecting data from each of the second time segments into a second data set; and
    filtering, from the first and second data sets, a contribution to the first and second data sets arising from background neural activity.

9. The method of claim 8, wherein filtering comprises performing a correlation between data representative of the background neural activity and the first and second data sets.

10. The method of claim 8, wherein filtering comprises performing a t-test between data representative of the background neural activity and the first and second data sets.

11. A drug screen method for identifying a candidate drug for the treatment of Alzheimer's disease, the method comprising:
    administering a test compound to test subjects;
    having the test subjects perform a sustained N-back task;
    imaging the subjects, and operating a data-processing system comprising a processor configured to:
        determine a first evolution of neural activity in the test subjects based on the subjects images;
        compare the first evolution of neural activity with a second evolution of neural activity, wherein the second evolution of neural activity is obtained from control subjects performing the sustained N-back tasks in the absence of the test compound, and
        designate the test compound as a candidate drug when a difference between the first and second evolutions of neural activity is above a different threshold.

* * * * *

UNITED STATES PATENT AND TRADEMARK OFFICE
CERTIFICATE OF CORRECTION

PATENT NO. : 7,658,912 B2
APPLICATION NO. : 10/871745
DATED : February 9, 2010
INVENTOR(S) : Paskavitz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1376 days.

Signed and Sealed this

Thirtieth Day of November, 2010

David J. Kappos
*Director of the United States Patent and Trademark Office*